United States Patent
Tezuka et al.

(10) Patent No.: US 8,958,858 B2
(45) Date of Patent: Feb. 17, 2015

(54) LIVING-BODY COMPONENT MEASURING APPARATUS

(75) Inventors: Shin-ichiro Tezuka, Musashino (JP); Hitoshi Hara, Musashino (JP)

(73) Assignee: Yokogawa Electric Corporation, Musashino-shi (JP)

( * ) Notice: Subject to any disclaimer, the term of this patent is extended or adjusted under 35 U.S.C. 154(b) by 351 days.

(21) Appl. No.: 13/041,105

(22) Filed: Mar. 4, 2011

(65) Prior Publication Data

US 2011/0218412 A1  Sep. 8, 2011

(30) Foreign Application Priority Data

Mar. 4, 2010  (JP) ................................. 2010-047723

(51) Int. Cl.
*A61B 5/1455* (2006.01)
*A61B 5/145* (2006.01)
*G01N 21/49* (2006.01)

(52) U.S. Cl.
CPC ........... *A61B 5/1455* (2013.01); *A61B 5/14532* (2013.01); *G01N 21/49* (2013.01); *A61B 2562/0242* (2013.01)
USPC ............ 600/310; 600/316; 600/322; 600/473

(58) Field of Classification Search
USPC ......... 600/310, 316, 322, 323, 331, 336, 473, 600/476
See application file for complete search history.

(56) References Cited

U.S. PATENT DOCUMENTS

| | | | | |
|---|---|---|---|---|
| 4,136,566 A | * | 1/1979 | Christensen .................. | 374/161 |
| 4,653,498 A | * | 3/1987 | New et al. ..................... | 600/324 |
| 5,305,759 A | * | 4/1994 | Kaneko et al. ................. | 600/476 |
| 5,353,790 A | * | 10/1994 | Jacques et al. ................ | 600/315 |
| 5,638,816 A | * | 6/1997 | Kiani-Azarbayjany et al. .............................. | 600/316 |
| 5,969,815 A | * | 10/1999 | Toida et al. .................... | 600/316 |
| 6,067,463 A | * | 5/2000 | Jeng et al. ..................... | 600/336 |
| 7,003,337 B2 | * | 2/2006 | Harjunmaa et al. .......... | 600/322 |
| 2004/0127778 A1 | * | 7/2004 | Lambert et al. ............... | 600/318 |

FOREIGN PATENT DOCUMENTS

JP  2008-301944 A  12/2008

OTHER PUBLICATIONS

Miyauchi, Yuki et al "Development of Noninvasive Blood Glucose Measuring Instrument by Near-Infrared Confocal Optical System," 8th Symposium of the Japanese Society for Medical and Biological Engineering, Apr. 23, 2009, p. 7-8.
Miyauchi, Yuki et al "Noninvasive measurement of blood glucose level with use of near-infrared confocal laser," 48th Meeting of the Japan Society for Medical and Biological Engineers, Apr. 2009, p. 148.
Miyauchi, Yuki et al "Non-invasive method for measuring blood sugar level by confocal optical system with near-infrared laser" Symposium of Medicine and Biology 2009, Sep. 2009, p. 387.

* cited by examiner

*Primary Examiner* — Tse Chen
*Assistant Examiner* — Chu Chuan (JJ) Liu
(74) *Attorney, Agent, or Firm* — Westerman, Hattori, Daniels & Adrian, LLP

(57) ABSTRACT

A living-body component measuring apparatus measures a component of an inner tissue of a living body serving as an object to be measured by emitting laser light having two or more wavelengths from a light source and measuring reflected light of the laser light from the inner tissue of the living body. The living-body component measuring apparatus includes a beam splitter that changes optical paths of a part of the laser light and the reflected light, a reference-light measuring unit that measures, as reference light, the part of the laser light having the optical path changed by the beam splitter, a reflected-light measuring unit that measures the reflected light having the optical path changed by the beam splitter, and an analysis unit that analyzes the inner tissue by measuring a spectrum of the reflected light or the reference light.

15 Claims, 7 Drawing Sheets

LIVING-BODY COMPONENT MEASURING APPARATUS

BACKGROUND OF THE INVENTION

1. Field of the Invention

The present disclosure relates to a living-body component measuring apparatus that measures a component of the inner tissue of a living body by measuring reflected light of laser light having two or more wavelengths emitted from a light source, and more particularly, to a living-body component measuring apparatus that is improved to more accurately and more stably determine the quantity of a substance in the living body.

2. Description of the Related Art

For example, in a spectroscopy method of the related art using near-infrared light, when light is applied from a light source to an object to be measured, a component contained in the object exhibits an optical absorption characteristic based on the quantity of the component in a wavelength region peculiar to the component. Hence, an absorbance (light absorbance of a specific component) is calculated from measurement light such as reflected light from the object, and the component contained in the object is analyzed on the basis of the absorbance spectrum.

Japanese Unexamined Patent Application Publication No. 2008-301944 proposes a living-body component measuring apparatus that measures components of the inner tissue of the living body (e.g., various substances contained in the blood in a blood vessel or tissue fluid in the tissue of the human body and animals (the concentration of a component such as the blood sugar level)) with a wavelength tunable laser and a confocal optical system. This living-body component measuring apparatus measures components of the inner tissue of the living body serving as an object to be measured by measuring reflected light from the inner tissue of the living body and light passing through the living body, which are obtained from laser light emitted from the wavelength tunable laser and having two or more wavelengths.

More specifically, laser light having two or more wavelengths is applied onto the inner tissue of a living body serving as an object to be measured, and the absorbance spectrum is obtained from light reflected from the inner tissue of the living body and light passing through the living body. After that, components of the inner tissue of the living body are calculated by a known test, and an expression representing the correlation between the absorbance spectrum and the components of the inner tissue of the living body (hereinafter referred to as a correlation expression) is created and stored beforehand. By substituting the absorbance calculated from the reflected light from the inner tissue of the living body and the light passing through the living body into the correlation expression, a component of the inner tissue of the living body is measured.

The living-body component measuring apparatus of the above publication further includes a movement driving mechanism that three-dimensional moves the confocal optical system and the living body relative to each other. By three-dimensional moving the confocal optical system and the living body relative to each other by the movement driving mechanism, the focal position of the confocal optical system is three-dimensional moved relative to the living body, and three-dimensional data on the inner tissue of the living body is obtained, whereby a portion of the living body to be measured is reliably specified, and a component of the portion of the living body is reliably measured in a non-invasive manner.

Such a living-body component measuring apparatus of the related art can measure the concentration of a target component on the basis of a degree (absorbance) to which light applied to the living body is absorbed by the living body, by detecting reflected light from the living body and light passing through the living body, without collecting the blood by invading the living body (more specifically, without actually collecting the blood by finger stick or earlobe stick).

In the living-body component measuring apparatus of the related art, however, the change in intensity of output light from the wavelength tunable laser leads to the change in intensity of scattering light in the living body. This makes it difficult to substantially remove errors due to this change.

That is, the living-body component measuring apparatus of the related art cannot accurately measure the absorbance spectrum since the intensity of output light from the wavelength tunable laser changes.

SUMMARY OF THE INVENTION

Accordingly, the present disclosure realizes a living-body component measuring apparatus that can accurately and stably determine the quantity of a substance in a living body.

To achieve this, a living-body component measuring apparatus according to a first aspect of the present disclosure measures a component of an inner tissue of a living body serving as an object to be measured by emitting laser light having two or more wavelengths from a light source and measuring reflected light of the laser light from the inner tissue of the living body. The living-body component measuring apparatus includes: a beam splitter that changes optical paths of a part of the laser light emitted from the light source and the reflected light from the inner tissue of the living body; a reference-light measuring unit that measures, as reference light, the part of the laser light emitted from the light source and having the optical path changed by the beam splitter; a reflected-light measuring unit that measures the reflected light reflected by the inner tissue of the living body and having the optical path changed by the beam splitter; and analysis unit that analyzes the inner tissue of the living body by measuring a spectrum of the reflected light or the reference light.

Preferably, the reference-light measuring unit includes light collector that collects the reference light having the optical path changed by the beam splitter; a pinhole that transmits the reference light collected by the light collector; a first light receiving element that receives the reference light transmitted through the pinhole and outputs a data signal based on an amount of the received reference light; and an A/D converter that subjects the data signal to A/D conversion and outputs the converted data signal to the analysis unit.

Preferably, the living-body component measuring apparatus further includes a movement driving mechanism that three-dimensional moves the reflected-light measuring unit and the living body relative to each other so that a focal position of the reflected-light measuring unit is three-dimensional moved relative to the living body to obtain three-dimensional data on the inner tissue of the living body.

A living-body component measuring apparatus according to a second aspect of the present disclosure measures a component of an inner tissue of a living body serving as an object to be measured by emitting laser light having two or more wavelengths from a light source onto the living body and measuring reflected light from the inner tissue of the living body. The living-body component measuring apparatus includes a branching unit that branches the laser light emitted from the light source; a reference-light measuring unit that measures, as reference light, one part of the laser light branched by the branching unit; a reflected-light measuring unit that measures the other part of the laser light branched by the branching unit and serving as the reflected light from the inner tissue of the living body; and analysis unit that analyzes the inner tissue of the living body by measuring a spectrum of the reflected light or the reference light serving as the part of the laser light branched by the branching unit.

A living-body component measuring apparatus according to a third aspect of the present disclosure measures a component of an inner tissue of a living body serving as an object to be measured by emitting laser light having two or more wavelengths from a light source and measuring reflected light of the laser light from the inner tissue of the living body. The living-body component measuring apparatus includes a first beam splitter that transmits one part of the laser light emitted from the light source and changes an optical path of the other part of the laser light; a second beam splitter that changes an optical path of the part of the laser light incident through the first beam splitter, transmits the other part of the laser light, and changes an optical path of the reflected light from the inner tissue of the living body; a reference-light measuring unit that measures, as reference light, the other part of the laser light emitted from the light source and having the optical path changed by the first beam splitter; a reflected-light measuring unit that measures the reflected light reflected by the inner tissue of the living body and having the optical path changed by the second beam splitter; and an analysis unit that analyzes the inner tissue of the living body by measuring a spectrum of the reflected light or the reference light having the optical path changed by the first beam splitter.

Preferably, the living-body component measuring apparatus further includes an optical fiber that applies the laser light emitted from the light source onto a surface of the living body; a second light receiving element that detects reflected light of the laser light applied by the optical fiber, the reflected light being reflected by the surface of the living body; and a light-source driving circuit that drives the light source on the basis of a detection signal from the second light receiving element so that an intensity of the laser light emitted from the light source is kept at a predetermined value.

Preferably, the analysis unit measures the component of the inner tissue on the basis of data standardized by dividing the detection signal for the reflected light from the inner tissue by the detection signal from the second light receiving element.

Preferably, the light source incorporates a third light receiving element that monitors the laser light emitted from the light source, and the light-source driving circuit drives the light source on the basis of at least one of the detection signal from the second light receiving element and a detection signal from the third light receiving element so that the intensity of the laser light emitted from the light source is kept at the predetermined value.

Preferably, the light source incorporates a third light receiving element that monitors the laser light emitted from the light source, and the analysis unit measures the component of the inner tissue on the basis of data standardized by dividing the detection signal for the reflected light from the inner tissue by at least one of the detection signal from the second light receiving element and a detection signal from the third light receiving element.

Preferably, the light source incorporates a third light receiving element that monitors the laser light emitted from the light source, and the analysis unit measures the component of the object on the basis of data obtained by linearly combining a first standardized signal obtained by dividing the detection signal for the reflected light from the inner tissue by the detection signal from the second light receiving element and a second standardized signal obtained by dividing the detection signal for the reflected light from the inner tissue by a detection signal from the third light receiving element.

Preferably, the light-source driving circuit drives the light source on the basis of at least one of the detection signal from the second light receiving element, the detection signal from the third light receiving element, and a detection signal for the reference light so that the intensity of the laser light from the light source is kept at the predetermined value.

Preferably, the analysis unit measures the component of inner tissue on the basis of data standardized by dividing the detection signal for the reflected light from the inner tissue by at least one of the detection signal from the second light receiving element, the detection signal from the third light receiving element, and the detection signal for the reference light.

Preferably, the analysis unit measures the component of the inner tissue on the basis of data obtained by linearly combining signals standardized by dividing the detection signal for the reflected light from the inner tissue by the detection signal from the second light receiving element, the detection signal from the third light receiving element, and the detection signal for the reference light.

Thus, the living-body component measuring apparatus according to the first aspect of the present disclosure includes the beam splitter that changes optical paths of a part of laser light emitted from the light source and reflected light from the inner tissue of the living body, the reference-light measuring unit that measures, as reference light, the part of the laser light emitted from the light source and having the optical path changed by the beam splitter, and the analysis that analyzes the inner tissue of the living body by measuring a spectrum of the reflected light or the reference light. This allows a more accurate and more stable determination of the quantity of the substance in the living body than in the related art.

The living-body component measuring apparatus of the second aspect of the present disclosure includes the branching unit that branches the laser light emitted from the light source, and the analysis unit that analyzes the inner tissue of the living body by measuring the spectrum of reflected light or reference light serving as the laser light branched by the branching unit. This allows more accurate and more stable determination of the quantity of the substance in the living body than in the related art.

The living-body component measuring apparatus according to the third aspect of the present disclosure includes the first beam splitter that transmits one part of the laser light emitted from the light source and changes the optical path of the other part of the laser light, the second beam splitter that changes an optical path of the part of the laser light incident through the first beam splitter, transmits the other part of the laser light, and changes an optical path of the reflected light from the inner tissue of the living body, and the analysis unit that analyzes the inner tissue of the living body by measuring the spectrum of the reflected light or the reference light having the optical path changed by the first beam splitter. This allows a more accurate and more stable determination of the quantity of the substance in the living body than in the related art.

DESCRIPTION OF THE EMBODIMENTS

The present disclosure relates to a living-body component measuring apparatus that measures a component of the inner tissue of a living body serving as an object to be measured by applying laser light having two or more wavelengths emitted from a light source onto the living body and measuring reflected light from the inner tissue of the living body. More particularly, the present disclosure relates to a living-body component measuring apparatus that more accurately and more stably determines the quantity of the substance in the living body. Living-body component measuring apparatuses according to embodiments of the present disclosure will be described below with reference to the drawings.

First Embodiment

Figure 1:
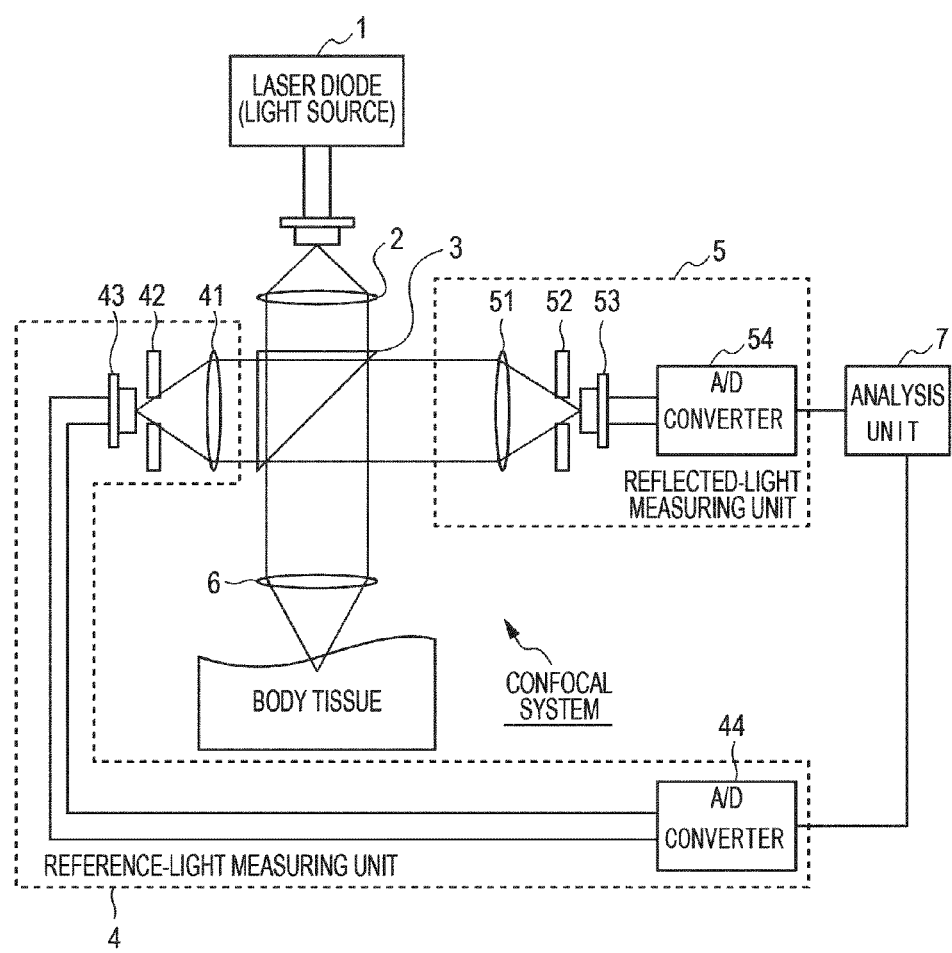
FIG. 1 is a structural view of a living-body component measuring apparatus according to a first embodiment of the present disclosure.

FIG. 1 is a structural view of a living-body component measuring apparatus according to a first embodiment of the present disclosure. The living-body component measuring apparatus illustrated in FIG. 1 is characterized as follows. A beam splitter changes the optical paths of a part of laser light emitted from a light source, such as a wavelength tunable laser or a wavelength fixed laser, and reflected light from the inner tissue of a living body, a reference-light measuring unit measures, as reference light, the laser light emitted from the light source and having the optical path changed by the beam splitter, and an analysis unit analyzes the inner tissue of the living body by measuring the spectrum of the reflected light or the reference light.

Configuration

Referring to FIG. 1, the living-body component measuring apparatus of the first embodiment mainly includes a laser diode 1 such as a wavelength tunable laser or a wavelength fixed laser, a lens 2, a prism 3, a reference-light measuring unit 4, a reflected-light measuring unit 5, an objective lens 6, and an analysis unit 7. The laser diode 1 serves as an example of a light source that outputs infrared light to be applied to the inner tissue of the living body. The lens 2 is formed by a collimator lens serving as an example of a collimating unit that collimates laser light from the laser diode 1. The prism 3 serves as an example of a beam splitter that changes the optical paths of a part of the laser light emitted from the laser diode 1 and collimated by the lens 2 and reflected light from the inner tissue of the living body. The reference-light measuring unit 4 measures, as reference light, the laser light emitted from the light source and having the optical path changed by the prism 3. The reflected-light measuring unit 5 measures the reflected light reflected by the inner tissue of the living body and having the optical path changed by the prism 3. The objective lens 6 serves as an example of a lens system including an objective lens. The objective lens 6 collects the light passing through the prism 3 and applies the collected light to the inner tissue of the living body, and collimates the reflected light from the inner tissue of the living body and directs the collimated reflected light to the prism 3. The analysis unit 7 analyzes the inner tissue of the living body by measuring the spectrum of the reflected light or the reference light. The analysis unit may be a personal computer running specialized software, or may be a specially made computer for the purpose of performing the analysis, or any other suitable computing device.

Although not particularly illustrated, the living-body component measuring apparatus of the first embodiment includes a table on which a living body, such as an arm of a subject, is placed. For example, the arm of the subject is placed as the living body, and the laser diode 1 is located above the arm of the subject.

The laser diode 1 adopted in the living-body component measuring apparatus of the first embodiment may be formed by a wavelength tunable laser. Instead of using the wavelength tunable laser, switching may be made between a plurality of lasers that emit laser beams having different wavelengths.

The reference-light measuring unit 4 includes a lens 41, a first pinhole 42, a light-receiving element 43, and an A/D converter 44. The lens 41 serves as an example of a first light collector that collects part of laser light emitted from the laser diode 1 and having the optical path changed by the prism 3 (light leaking out from the prism 3). The first pinhole 42 is provided on the optical axis of the lens 41 so as to transmit the reference light collected by the lens 41. The light-receiving element 43 is formed by, for example, a photomultiplier tube, a photodiode, or a charge coupled device (CCD). The light-receiving element 43 receives the reference light transmitted through the first pinhole 42 and outputs a data signal based on the amount of received light. The A/D converter 44 is electrically connected to the light-receiving element 43. The A/D converter 44 receives the output signal from the light-receiving element 43 and subjects the output signal to analog-to-digital (A/D) conversion.

The reflected-light measuring unit 5 includes a lens 51, a second pinhole 52, a light-receiving element 53, and an A/D converter 54. The lens 51 serves as an example of a second light collector that collects the reflected light whose optical path is changed by the prism 3. The second pinhole 52 is provided on the optical axis of the lens 51 so as to transmit the reflected light collected by the lens 51. The light-receiving element 53 is formed by, for example, a photomultiplier tube, a photodiode, or a CCD. The light-receiving element 53 receives the reflected light transmitted through the second pinhole 52 and outputs a data signal based on the amount of received light. The A/D converter 54 is electrically connected to the light-receiving element 53. The A/D converter 54 receives the output signal from the light-receiving element 53 and subjects the output signal to A/D conversion.

The amount of reflected light transmitted through each of the first and second pinholes 42 and 52 can be adjusted by adding an un-illustrated stop or switching a plurality of pinholes having different diameters.

The analysis unit 7 is formed by a computer in which a central processing unit (CPU), a read only memory (ROM), a random access memory (RAM), an input/output interface, etc. are connected to a bus. The CPU reads out various programs stored in the ROM, for example, a data analysis program, and appropriately expands the programs in the RAM so as to perform various processing operations.

The analysis unit 7 measures the changes in light amount of the reference light and the reflected light on the basis of the output signals from the A/D converter 44 and 54. Also, the analysis unit 7 corrects the changes in light amount obtained from the A/D converter 54 in correspondence to the wavelengths of the reflected light from the inner tissue of the living body on the basis of the changes in light amount obtained from the A/D converter 44 in correspondence to the wavelengths of the reference light, thereby calculating the amount of attenuation due to absorption by the inner tissue of the living body and analyzing components contained in the inner tissue of the living body on the basis of the absorbance spectrum.

More specifically, the analysis unit 7 stores a correlation expression (calibration curve) representing the correlation between the absorbance spectrum and various components of the inner tissue of the living body, and the components of the inner tissue are measured and analyzed by substituting the absorbance calculated from the reflected light from the inner tissue into the correlation expression.

Operations

The living-body component measuring apparatus of the first embodiment having the above-described configuration performs the following Operations 1-1 to 1-12 and 2-1 to 2-6.

Operation 1-1

The laser diode 1 emits laser light.

When the laser diode 1 is a wavelength tunable laser, measurement of reflected light and reference light may be continued by intermittently performing the following Operations 1-1 to 1-12 and 2-1 to 2-6 according to a predetermined schedule or timing while changing the wavelength of the emitted laser light.

Operation 1-2

The laser light from the laser diode 1 is converted into parallel light by the lens 2, and then enters the prism 3.

The parallel light incident on the prism 3 is split into one part of light that passes through the prism 3 and is applied to the living body and the other part of light whose optical path is changed by reflection of the prism 3 toward the reference-light measuring unit 4.

The following operations 1-3 and subsequent operations are performed for the light passing through the prism 3, and the following operations 2-1 to 2-6 are performed for the light whose optical path is changed by the prism 3 toward the reference-light measuring unit.

Operation 1-3

The incident parallel light passes through the prism 3 and enters the objective lens 6.

Operation 1-4

The objective lens 6 converges the incident parallel light at the living body (inner tissue of the living body).

Operation 1-5

The objective lens 6 converts reflected light from the inner tissue of the living body into parallel light and directs the parallel reflected light to the prism 3.

The reflected light is absorbed by the inner tissue of the living body, so that a part of light with a specific wavelength, of the light emitted from the laser diode 1, attenuates.

Operation 1-6

The prism 3 reflects the incident reflected light toward the lens 51.

Operation 1-7

The lens 51 collects the reflected light from the prism 3 at the second pinhole 52. The lens 51 is located at a position such that the reflected light from the prism 3 converges at the second pinhole 52 and passes through the second pinhole 52.

Operation 1-8

The reflected light converged at the second pinhole 52 passes through the second pinhole 52 and enters the light-receiving element 53.

Operation 1-9

The light-receiving element 53 receives the reflected light passing through the second pinhole 52, and outputs a data signal based on the amount of received light.

Operation 1-10

The A/D converter 54 subjects the output signal from the light-receiving element 53 to A/D conversion, and outputs a data signal based on the amount of reflected light received by the light-receiving element 53 to the analysis unit 7.

Operation 1-11

The analysis unit 7 receives the data signal indicating the light intensity of the reflected light from the A/D converter 54, and detects the spectrum of the reflected light.

Operation 1-12

The analysis unit 7 corrects the changes in light amount obtained in Operation 1-11 in correspondence to the wavelengths of the reflected light from the inner tissue of the living body on the basis of the changes in light amount obtained in later Operation 2-6 in correspondence to the wavelengths of reference light, thereby calculating the amount of attenuation due to absorption by the inner tissue of the living body and analyzing components contained in the inner tissue of the living body on the basis of the absorbance spectrum.

More specifically, various components of the inner tissue of the living body are measured and analyzed by substituting the absorbance calculated from the reflected light from the inner tissue into a correlation expression (calibration curve) pre-stored in the analysis unit 7 and indicating the correlation between the absorbance spectrum and various components of the inner tissue.

Also, the analysis unit 7 measures scattering light and reflected light at different wavelengths (e.g., an absorption wavelength for a target substance and a wavelength that is rarely absorbed) by the above-described optical system, and performs component analysis (e.g., measurement of blood sugar level) using a correlation expression (calibration curve) relating to absorption by a certain component (e.g., glucose) in the inner tissue of the living body.

When the distance between the analysis unit 7 and the living body is long, the reflected light is guided from the light-receiving element 53 to the A/D converter 54 via a first light guide unit (not illustrated) such as an optical fiber. Hence, there are influences of the material and length of the light guide unit and the environment such as ambient temperature change.

For this reason, a second light guide unit (not illustrated) for guiding the reference light from the light-receiving element 43 to the A/D converter 44 may be laid along the same route as that of the first light guide unit for the reflected light so that the reference light also receives influences equivalent to the influences on the measurement light.

The reference light is not influenced by absorption of the inner tissue of the living body, but is influenced only by the setting condition of the second light guide unit and surrounding environment. Therefore, the analysis unit 7 corrects the changes in light amount in correspondence to the wavelengths of the reflected measurement light from the inner tissue of the living body on the basis of the changes in light amount in correspondence to the wavelengths of the reference light. Thus, the analysis unit 7 can calculate the amount of attenuation due to absorption by the inner tissue and analyze components contained in the inner tissue on the basis of the absorbance spectrum.

Operation 2-1

The part of light, whose optical path is changed by the prism 3 toward the reference-light measuring unit 4, enters the lens 41 in the reference-light measuring unit 4.

The living-body component measuring apparatus of the first embodiment uses this light as reference light for analysis of substances in the living body. The reference light is used as a target for comparison when the analysis unit 7 detects the degree of attenuation of the light due to reflection by the inner tissue of the living body.

Operation 2-2

The lens 41 collects the incident light at the first pinhole 42. The lens 41 is located at a position such that the reference light from the prism 3 converges at the first pinhole 42 and passes through the first pinhole 42.

Operation 2-3

The collected reference light passes through the first pinhole 42, and enters the light-receiving element 43.

Operation 2-4

The light-receiving element 43 receives the reference light passing through the first pinhole 42, and outputs a data signal based on the amount of received light.

Operation 2-5

The A/D converter 44 subjects the output signal from the light-receiving element 43 to A/D conversion, and outputs a data signal based on the amount of reference light received by the light-receiving element 43 to the analysis unit 7.

Operation 2-6

The analysis unit 7 receives the data signal from the A/D converter 44 indicating the light intensity of the reference light, and detects the spectrum of the reference light.

When the laser diode 1 is a wavelength tunable laser as an example, the living-body component measuring apparatus of the first embodiment intermittently performs the above-described Operations 1-1 to 1-12 and 2-1 to 2-6 according to the predetermined schedule or timing while changing the wavelength of the laser light to be emitted, and continues measurement of the reflected light and the reference light.

Thus, the living-body component measuring apparatus of the first embodiment includes the beam splitter that changes the optical paths of a part of laser light emitted from the light source and reflected light from the inner tissue of the living body, the reference-light measuring unit that measures, as reference light, the part of laser light emitted from the light source and having the optical path changed by the beam splitter, and the analysis unit that analyzes the inner tissue of the living body by measuring the spectrum of the reflected light or the reference light. This allows the living-body component measuring apparatus to more accurately and more stably determine the quantity of the substance in the living body than the related art.

Moreover, since the living-body component measuring apparatus of the present disclosure uses the laser light and the confocal system, it can receive almost all light scattering in the living body, of the light emitted for spectrum formation, and can use the received light for signal processing.

Positioning in x-, y-, and z-axis Directions

In the living-body component measuring apparatus of the present disclosure, the lens system may be movable in the depth direction (z-axis direction) so as to change the focal position in the object. Further, the living-body component measuring apparatus of the present disclosure may include a mechanism that can perform scanning in the x- and y-axis directions so as to obtain three-dimensional information about the interior of the living body (interior of skin tissue).

For example, the living-body component measuring apparatus of the present disclosure may include an unillustrated movement driving mechanism that three-dimensional moves a confocal optical system including the above-described objective lens 6 and so on and the living body relative to each other. The focal position of the confocal optical system is three-dimensional moved relative to the living body by driving the movement driving mechanism, so that three-dimensional data on the inner tissue of the living body can be obtained.

More specifically, in the first embodiment, the operator can actuate the movement driving mechanism by operating the computer that forms the analysis unit 7. By the operation of the movement driving mechanism, the laser diode 1, the lens 2, the prism 3, the objective lens 6, the lens 51, the second pinhole 52, and the light-receiving element 53 in the confocal optical system are finely moved together in the three-dimensional direction, that is, in the x-, y-, and z-axis directions on the order of micrometers relative to the living body placed on the un-illustrated table.

Here, the x-axis direction and the y-axis direction are orthogonal to each other in a plane substantially parallel to an epidermis surface of the living body. Hereinafter, the x-axis direction and the y-axis direction will be collectively referred to as a planar direction parallel to the epidermis surface of the living body or simply referred to as a planar direction. The z-axis direction is orthogonal to the x-axis direction and the y-axis direction, and indicates the depth from the epidermis surface of the living body. Hereinafter, the z-axis direction will be referred to as a direction of the depth from the epidermis surface of the living body or simply referred to as a depth direction.

That is, in the first embodiment, the movement driving mechanism moves the above-described components of the confocal optical system in minute steps in the x-axis direction and the y-axis direction, that is, in the planar direction parallel to the epidermis surface of the living body according to instructions from the CPU in the computer that forms the analysis unit 7 on the basis of the operation of a keyboard or the like by the operator, whereby the focal position F of the objective lens 6 in the confocal optical system can be two-dimensionally scanned in the planar direction in the inner tissue of the living body.

Further, the movement driving mechanism moves the components of the confocal optical system in small steps in the z-axis direction, that is, in the depth direction according to the instructions from the CPU based on the operation of the operator, so that the focal position F of the objective lens 6 in the confocal optical system can be moved in minute steps in the depth direction.

Accordingly, by two-dimensionally scanning the focal position F in the planar direction while changing the depth in the living body, three-dimensional data on the inner tissue of the living body can be acquired.

The living-body component measuring apparatus of the present disclosure having the above-described configuration performs the following operations so as to position the lens system in the depth direction (z-axis direction) and the x- and y-directions and to acquire three-dimensional information about the interior of the living body (interior of the skin tissue).

As an example of an operation of the present disclosure, a description will be given below of a case in which, for example, the dermis tissue of the arm of the subject is irradiated with laser light by the living-body component measuring apparatus, the absorbance of the laser light by glucose in the blood of the subject is measured on the basis of data on reflected light received by the light-receiving element, and the blood sugar level is determined.

For example, in the living-body component measuring apparatus of the present disclosure, data on the glucose concentration of an illustrated dermis tissue a2, of the inner tissues of the living body, is three-dimensional collected, a capillary existing in the dermis tissue a2 is located, and the glucose concentration at the capillary is measured as the glucose concentration of the blood, that is, the blood glucose level.

For that purpose, first, the position of the dermis tissue a2 in the living body is specified while moving the confocal optical system in the z-axis direction, that is, in the direction of depth from the epidermis surface of the living body.

An epidermis tissue a1, the dermis tissue a2, and a subcutaneous tissue a3 that constitute the skin tissue of the living body are different in the absorbance of all components, including glucose, that is, the total absorbance including the absorbance of glucose, water, fat, etc. according to the wavelength of the laser light to be applied. For example, when the wavelength of the laser light is 1450 nm, the absorbance of the dermis tissue a2 is much higher than the absorbance of the epidermis tissue a1 and the subcutaneous tissue a3. Further, it is actually observed that, when the wavelength of the laser light is appropriately selected, the absorbance for the laser light clearly differs among the epidermis tissue a1, the dermis tissue a2, and the subcutaneous tissue a3.

Accordingly, in the living-body component measuring apparatus of the present disclosure, positioning is performed by the un-illustrated movement driving mechanism so that the focal position F of the objective lens 6 is placed at a position near the epidermis surface, and the absorbance of all components for the laser light is then measured at various positions while finely moving the confocal optical system in the z-axis direction so as to move the focal position F in the depth direction in minute steps. At a position where the absorbance greatly increases, it is determined that the focal position F moves from the epidermis tissue a1 into the dermis tissue a2. The confocal optical system is further moved in the z-axis direction, and it is determined that the focal position F moves from the dermis tissue a2 into the subcutaneous tissue a3 at a position where the absorbance greatly decreases, thereby specifying the region of the dermis tissue a2 in the depth direction.

Instead of using the absorbances of all components as in the first embodiment, the position of the dermis tissue a2 in the depth direction can be specified by the above-described change in glucose concentration. As described above, capillaries develop and the glucose concentration is higher in the dermis tissue a2 than in the epidermis tissue a1 which includes a horny layer and in which capillaries rarely develop and the subcutaneous tissue a3 that is mainly formed by fat tissue. For this reason, the region in the depth direction in which the glucose concentration is high can be specified as a position of the dermis tissue a2 in the depth direction.

Subsequently, the confocal optical system is moved in the x- and y-axis directions within the region in the depth direction determined as the dermis tissue a2, and the focal position F of the objective lens 6 is finely moved in the planar direction parallel to the epidermis surface of the living body and is two-dimensionally scanned in the dermis tissue a2 so as to measure the glucose concentration at various positions. When the glucose concentrations at the positions are two-dimensionally mapped, for example, an area where the glucose concentration is higher than in the surroundings is detected, as shown by a diagonally shaded area in the figure.

By performing this mapping using two-dimensional scanning while finely moving the focal position F in the depth direction (z-axis direction), a three-dimensional distribution of the glucose concentration can be obtained.

Although glucose easily penetrates from the capillary into the tissue, as described above, the glucose concentration in the capillary is higher than in the dermis tissue a2. Hence, an area where a higher glucose concentration than in the surroundings is linearly detected can be determined as a capillary in the dermis tissue a2.

Thus, in the first embodiment, the area where a higher glucose concentration than in the surroundings is linearly detected is determined as a capillary in the dermis tissue a2, and a position of the capillary is specified. The glucose concentration at the position of the capillary is measured as the blood sugar level in blood that flows through the capillary.

In the first embodiment, as described above, the region of the dermis tissue a2 in the depth direction can be specified on the basis of the absorbances of all components, such as glucose, water, and fat, and the glucose concentration, and the position of the capillary in the dermis tissue a2 can be specified on the basis of the glucose concentration. When the position of the capillary can be thus specified, the concentration of a component of the blood other than glucose can be measured at the position.

To measure the concentration of a component other than glucose in this way, similarly to the above-described manner for glucose, for example, it is necessary to create beforehand weighting constants for weighted addition of absorbances of the component calculated on the basis of data signals obtained by changing the wavelength within the wavelength region where the absorbance of the component is high, and a standard curve correlating the weighted-added absorbances and the component and to store the weighting constants and the standard curve in the ROM.

Further, since the position of a tissue portion other than the capillary in the dermis tissue a2 can be specified, concentrations of various components of the tissue portion other than the capillary in the dermis tissue a2 can be measured by a method similar to the above method. In addition, in the first embodiment, the epidermis tissue a1, the dermis tissue a2, and the subcutaneous tissue a3 are separately specified and measured. Hence, it is possible to measure various components in the tissues while accurately distinguishing the components among the tissues.

As described above, according to the living-body component measuring apparatus of the first embodiment, the confocal optical system using laser light with different wavelengths can specify the position in the depth direction and the planar direction in the inner tissue of the living body and can measure the living-body components. For this reason, for example, even if the thicknesses of the portions that constitute the inner tissue of the living body, that is, the thicknesses of the epidermis tissue a1 and the dermis tissue a2 are different among individuals, as in a case in which a component of the dermis tissue a2 is measured, the positional region of a target portion in the depth direction can be specified using the difference in absorbance among the portions. Hence, it is possible to reliably locate the target portion and to measure a component in the target portion of the living body.

Second Embodiment

Instead of the above-described configuration of the first embodiment, the living-body component measuring apparatus of the present disclosure may have a configuration such as to branch laser light emitted from the laser diode 1 into light to be applied to the living body and light used as reference light, to analyze the inner tissue of the living body by measuring the spectrum of reflected light or the reference light, and to more accurately and more stably determine the quantity of a substance in the living body than the related art.

The reference-light measuring unit 4 may have any structure that allows the analysis unit 7 to measure reference light.

Figure 2:
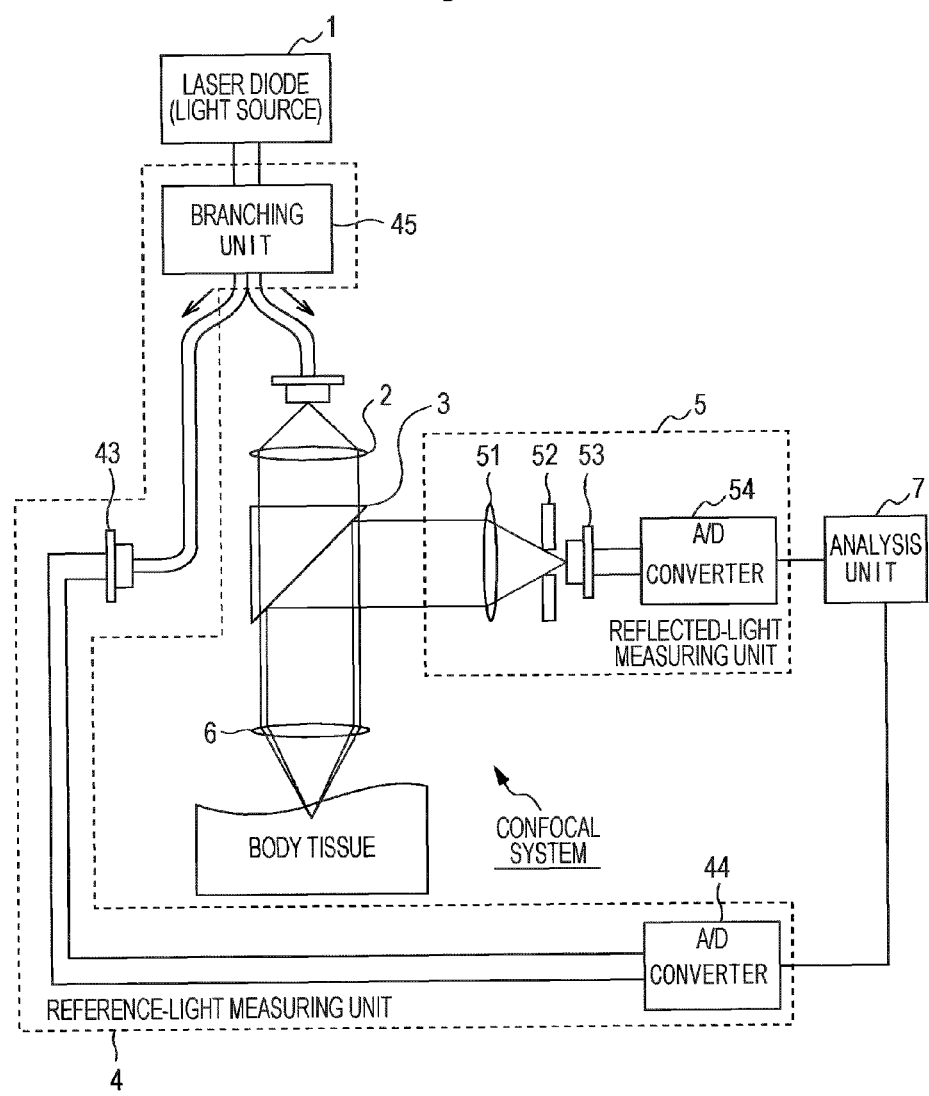
FIG. 2 is a structural view of a living-body component measuring apparatus according to a second embodiment of the present disclosure.

FIG. 2 is a structural view of a living-body component measuring apparatus according to a second embodiment of the present disclosure. In the following, descriptions of components common to FIG. 1 are appropriately omitted.

Referring to FIG. 2, a reference-light measuring unit 4 includes a branching unit 45 that branches light emitted from a laser diode 1, a light-receiving element 43 that receives a part of the light emitted from the laser diode 1 as reference light and outputs a data signal based on the amount of received light, and an A/D converter 44 electrically connected to the light-receiving element 43. The A/D converter 44 receives the output signal from the light-receiving element 43 and subjects the output signal to A/D conversion.

In this case, the living-body component measuring apparatus of the second embodiment performs the following operations.

(1) The laser diode 1 emits laser light.
(2) The light emitted from the laser diode 1 is branched by the branching unit 45 into "light to be applied to the living body" and "light used as reference light".
(3) The reference-light measuring unit 4 converts and outputs a data signal based on the amount of reference light serving as one part of the light branched by the branching unit 45.
(4) A reflected-light measuring unit 5 subjects, to A/D conversion, a data signal based on the amount of reflected light from the living body serving as the other part of the light branched by the branching unit 45.
(5) Similarly to the operation performed in the first embodiment, an analysis unit 7 corrects the changes in light amount in correspondence to the wavelengths of the reflected light from the inner tissue of the living body on the basis of the changes in light amount in correspondence to the wavelengths of the reference light, thereby calculating the amount of attenuation due to absorption by the inner tissue of the living body and analyzing components contained in the inner tissue of the living body on the basis of the absorbance spectrum.

Thus, the living-body component measuring apparatus of the second embodiment includes the branching unit that branches laser light emitted from the light source, and the analysis unit that analyzes the inner tissue of the living body by measuring the spectrum of reflected light or reference light serving as a part of the laser light branched by the branching unit. This allows the living-body component measuring apparatus to more accurately and more stably determine the quantity of the substances in the living body than the related art.

Third Embodiment

Instead of the configurations adopted in the above-described first and second embodiments, the living-body component measuring apparatus of the present disclosure may include a reference-light measuring unit having a first beam splitter, such as a prism, which transmits one part of laser light from a laser diode 1 and changes the optical path of the other part of the laser light from the laser diode 1, and a reflected-light measuring unit having a second beam splitter, such as a prism, which changes the optical path of one part of the laser light passing through the first beam splitter, transmits the other part of the laser light, and changes the optical path of reflected light from the inner tissue of the living body.

Figure 3:
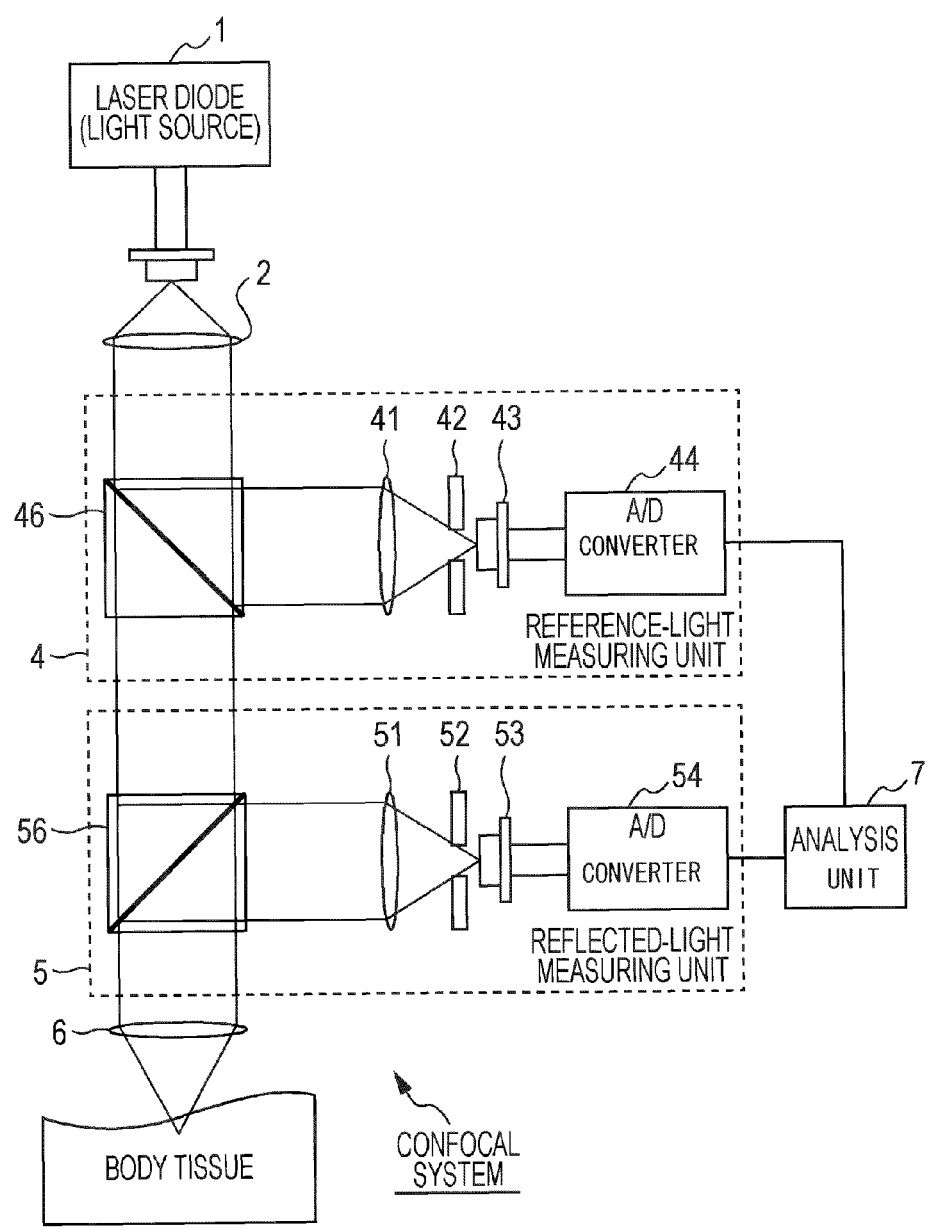
FIG. 3 is a structural view of a living-body component measuring apparatus according to a third embodiment of the present disclosure.

FIG. 3 is a structural view of a living-body component measuring apparatus according to a third embodiment of the present disclosure. In the following, descriptions of components common to FIG. 1 are omitted appropriately.

Referring to FIG. 3, the living-body component measuring apparatus of the third embodiment includes a laser diode 1, such as a wavelength tunable laser or a wavelength fixed laser, which outputs infrared light. The laser diode 1 serves as an example of a light source that emits light to the inner tissue of the living body. The living-body component measuring apparatus also includes a lens 2, such as a collimator lens, serving as an example of a collimating unit that converts laser light from the laser diode 1 into parallel light, a reference-light measuring unit 4, a reflected-light measuring unit 5, and an analysis unit 7.

In the living-body component measuring apparatus of the third embodiment, the reference-light measuring unit 4 includes a first beam splitter 46 that transmits one part of laser light incident from the laser diode 1 through the lens 2 and changes the optical path of the other part of the laser light from the laser diode 1, a lens 41 serving as an example of a first light collector that collects the laser light from the first beam splitter 46, a first pinhole 42 provided on the optical axis of the lens 41 so as to transmit the light collected by the lens 41, a light-receiving element 43 that receives the light emitted from the laser diode 1 as reference light and outputs a data signal based on the amount of received light, and an A/D converter 44 electrically connected to the light-receiving element 43. The A/D converter 44 receives the output signal from the light-receiving element 43 and subjects the output signal to A/D conversion.

In the living-body component measuring apparatus of the third embodiment, the reflected-light measuring unit 5 includes a second beam splitter 56 that changes the optical paths of a part of incident light from the first beam splitter 46 and reflected light from the inner tissue of the living body, a lens 51 serving as an example of a second light collector that collects the reflected light reflected by the inner tissue of the living body and received from the second beam splitter 56, a second pinhole 52 provided on the optical axis of the lens 51 so as to transmit the reflected light collected by the lens 51, a light-receiving element 53 that receives the reflected light and outputs a data signal based on the amount of received light, and an A/D converter 54 electrically connected to the light-receiving element 53. The A/D converter 54 receives the output signal from the light-receiving element 53 and performs subjects the output signal to A/D conversion.

In this case, the living-body component measuring apparatus of the third embodiment performs the following operations.

(1) The laser diode 1 emits laser light.
(2) One part of the laser light emitted from the laser diode 1 passes through the first beam splitter 46 and enters the second beam splitter 56 in the reflected-light measuring unit 5. The other part of the laser light emitted from the laser diode 1 is caused by the first beam splitter 46 to change the optical path thereof and enters the lens 41 in the reference-light measuring unit 4.
(3) The reference-light measuring unit 4 subjects, to A/D conversion, a data signal based on the amount of reference light serving as the other part of light split by the first beam splitter 46, and outputs the converted data signal.
(4) The reflected-light measuring unit 5 subjects, to A/D conversion, a data signal based on the amount of reflected light serving as the one part of light split by the first beam splitter 46 and reflected by the living body, and outputs the converted data signal.
(5) Similarly to the operation performed in the first embodiment, the analysis unit 7 corrects the changes in light amount in correspondence to the wavelengths of the reflected light from the inner tissue of the living body on the basis of the changes in light amount in correspondence to the wavelengths of the reference light, thereby calculating the amount of attenuation due to absorption by the inner tissue of the living body and analyzing components contained in the inner tissue of the living body on the basis of the absorbance spectrum.

The living-body component measuring apparatus of the third embodiment may include a block unit provided between the first and second beam splitter 46 and 56 so as to block the reflected light passing through the second beam splitter 56 and entering the first beam splitter 46 at a predetermined timing or at a predetermined measurement interval. For example, the block unit is formed by a rotary turret mechanism including filters or non-reflective plates.

In this case, for example, a computer that forms the analysis unit 7 controls the block unit so as to block the reflected light passing through the second beam splitter 56 and entering the first beam splitter 46 at a predetermined timing or a predetermined measurement interval stored in an un-illustrated storage.

Further, the computer that forms the analysis unit 7 controls the block unit so as to introduce the laser light passing through the first beam splitter 46 into the second beam splitter 56 at a predetermined timing.

This allows the living-body component measuring apparatus of the third embodiment to measure the substance in the living body on the basis of the reference light from the laser diode 1 that does not contain the reflected light passing through the second beam splitter 56.

Thus, the living-body component measuring apparatus of the third embodiment includes the first beam splitter that transmits one part of laser light emitted from the light source and changes the optical path of the other part of the laser light, the second beam splitter that changes the optical path of one part of the laser light incident through the first beam splitter, transmits the other part of the incident laser light, and changes the optical path of reflected light from the inner tissue of the living body, and the analysis unit that analyzes the inner tissue of the living body by measuring the spectrum of the reflected light or the reference light whose optical path is changed by the first beam splitter. This allows the living-body component measuring apparatus to more accurately and more stably determine the quantity of the substance in the living body than the related art.

In the above embodiments, stable measurement can be taken by driving the laser diode 1 in an automatic output control loop 8 so as to maintain a predetermined intensity of light applied from the laser diode 1 onto an object to be measured.

Figure 4:
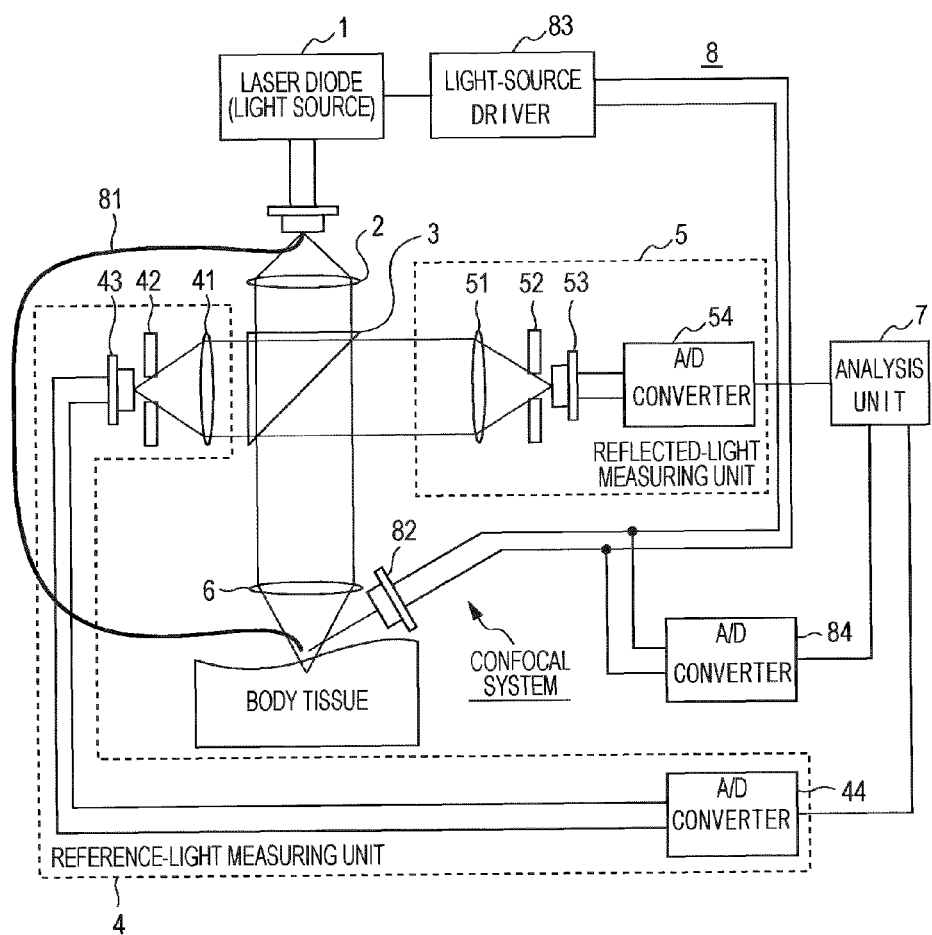
FIG. 4 is a structural view of a living-body component measuring apparatus according to a fourth embodiment of the present disclosure.

FIG. 4 is a structural view illustrating a fourth embodiment in which the above-described structure is applied to the first embodiment of FIG. 1. In the fourth embodiment of FIG. 4, a part of output light from a laser diode 1 is applied onto a surface of an object to be measured through an optical fiber 81, reflected light from the surface is detected by a second light receiving element 82, and an output signal from the second light receiving element 82 is transmitted to a light-source driver 83, whereby the laser diode 1 is driven to maintain a predetermined intensity of output light.

This reduces the change in intensity of output light resulting from the temperature change of the laser diode 1 and the spatial intensity change, and obtains a stable component measurement result.

Further, the output signal from the second light receiving element 82 is transmitted via an A/D converter 84 to an analysis unit 7, where an output signal from a light-receiving element 53 is standardized by being divided by the output signal from the second light receiving element 82. This compensates for the output change of the laser diode 1 and the change due to surface reflection of the object.

Figure 5:
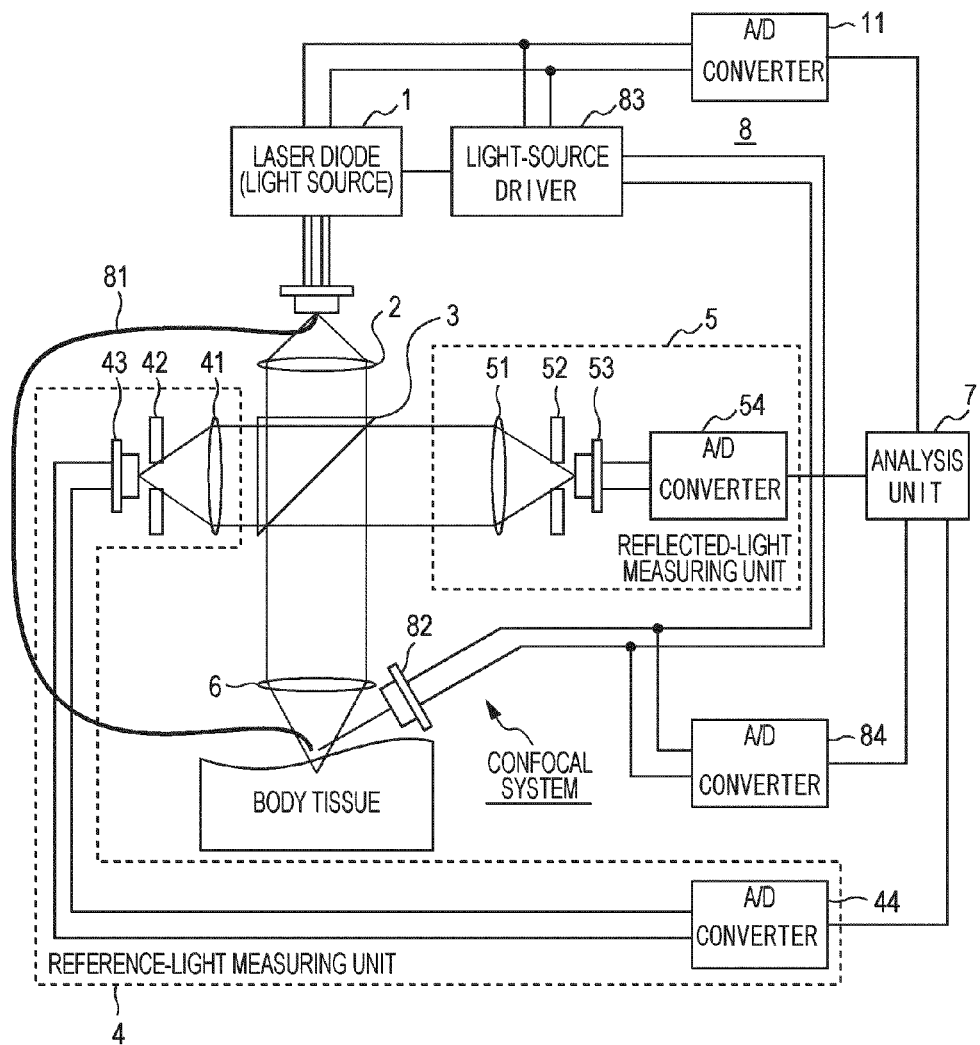
FIG. 5 is a structural view of a living-body component measuring apparatus according to a fifth embodiment of the present disclosure.

FIG. 5 is a structural view illustrating a fifth embodiment in which a laser diode 1 incorporates an un-illustrated third light receiving element for monitoring output light. An output signal from the third light receiving element is also input to a light-source driver 83, and the laser diode 1 is driven to maintain a predetermined intensity of output light.

The output signal from the third light receiving element is also input via an A/D converter 11 to an analysis unit 7, where an output signal from a light-receiving element 53 is standardized by being divided by the output signal from the third light receiving element. The analysis unit 7 linearly combines two standardized signals and obtains a combination coefficient by multivariate analysis. This accurately compensates for the output change of the laser diode 1 and the change due to surface reflection of the object on the basis of these values.

Figure 6:
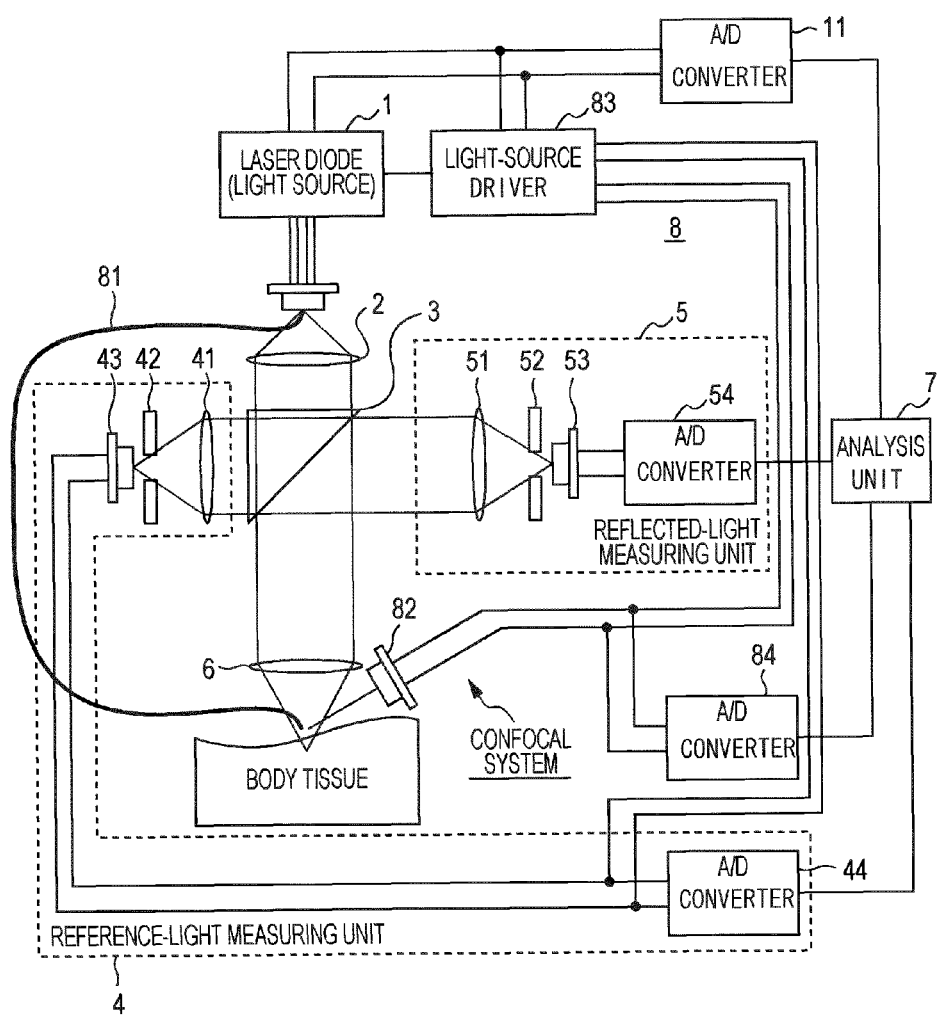
FIG. 6 is a structural view of a living-body component measuring apparatus according to a sixth embodiment of the present disclosure.

A sixth embodiment illustrated in FIG. 6 is different from the fifth embodiment of FIG. 5 in that an output signal from a light-receiving element 43 is also input to a light-source driver 83. The light-receiving element 43 detects the spatial change of output light from a laser diode 1, and the laser diode 1 is driven to maintain a predetermined intensity of output light.

Further, an output signal from a light-receiving element 53 is standardized by being divided by the output signal from the light-receiving element 43 input to an analysis unit 7 via an A/D converter 44. Thus, the analysis unit 7 linearly combines three standardized signals and obtains a combination coefficient by multivariate analysis. This accurately compensates for the output change and spatial change of the laser diode 1 and the change due to surface reflection of the object on the basis of these values.

Figure 7:
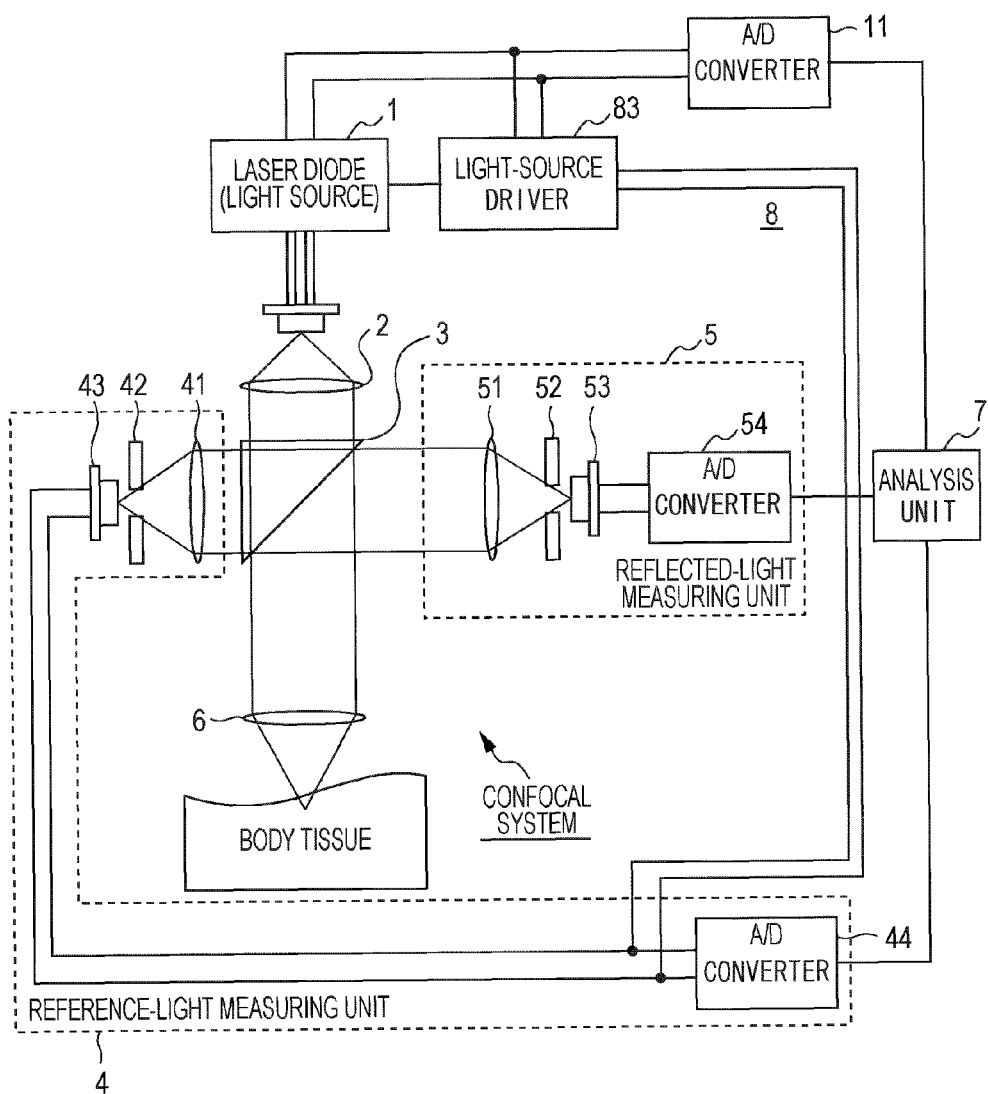
FIG. 7 is a structural view of a living-body component measuring apparatus according to a seventh embodiment of the present disclosure.

In a seventh embodiment illustrated in FIG. 7, the signal system including the optical fiber 81, the second light receiving element 82, and the A/D converter 84 adopted in the sixth embodiment of FIG. 6 is omitted. According to a configuration illustrated in FIG. 7, a light-source driver 83 drives a laser diode 1 on the basis of output signals from a third light receiving element and a light-receiving element 43 so as to maintain a predetermined intensity of output light. An analysis unit 7 accurately compensates for the output change and spatial change of the laser diode 1 on the basis of a signal standardized by dividing an output signal from a light-receiving element 53 by the output signal from the third light receiving element and a signal standardized by dividing the output signal from the light-receiving element 53 by the output signal from the light-receiving element 43.

While the laser diode 1 incorporates the third light receiving element for monitoring the output light in the embodiments of FIGS. 5 and 6, the third light receiving element may be omitted, as in the fourth embodiment of FIG. 4, depending on the compensation accuracy required of the apparatus.

In the embodiments of FIGS. 2 and 3, the output change of the laser diode 1 and the change due to surface reflection of the object can also be accurately compensated for by dividing the output signal from the light-receiving element 53 by the output signal from the light-receiving element 43 input to the analysis unit 7 via the A/D converter 44 for standardization.

Other Embodiments

The living-body component measuring apparatus of the present disclosure is applicable to overall technique relating to a living-body component measuring apparatus that measures components of the inner tissue of the living body (e.g., various substances contained in the blood in a blood vessel or tissue fluid in the tissue of the human body and animals (the concentration of a component such as the blood sugar level)) with a confocal optical system.

As described above, the living-body component measuring apparatus of the present disclosure can reduce errors and determine the quantity of the substance in the living body by separately receiving light (reference light) from the light source and calculating intensities of scattering light in the living body and the reference light.

What is claimed is:

1. A living-body component measuring apparatus that measures a component of an inner tissue of a living body serving as an object to be measured, the living-body component measuring apparatus comprising:
    a light source emitting laser light having two or more wavelengths;
    a beam splitter that changes optical paths of a part of the laser light emitted from the light source and a reflected light of the laser light from the inner tissue of the living body;
    a reference-light measuring unit that measures, as reference light, the part of the laser light emitted from the light source and having the optical path changed by the beam splitter into a first direction;
    a reflected-light measuring unit that measures the reflected light reflected by the inner tissue of the living body and having the optical path changed by the beam splitter into a second direction different from the first direction;
    an analysis unit that analyzes the inner tissue of the living body by measuring a spectrum of the reflected light and the reference light;
    an optical fiber that is configured to apply the laser light emitted from the light source onto a surface of the living body;
    a second light receiving element that detects reflected light of the laser light applied by the optical fiber in a third direction different from the first and second directions, the reflected light being reflected by the surface of the living body; and
    a light-source driving circuit that drives the light source on the basis of a detection signal from the second light receiving element so that an intensity of the laser light emitted from the light source is kept at a predetermined value.

2. The living-body component measuring apparatus according to claim 1, wherein the reference-light measuring unit includes:
    a light collector that collects the reference light having the optical path changed by the beam splitter;
    a pinhole that transmits the reference light collected by the light collector;
    a first light receiving element that receives the reference light transmitted through the pinhole and outputs a data signal based on an amount of the received reference light; and
    an A/D converter that subjects the data signal to A/D conversion and outputs the converted data signal to the analysis unit.

3. The living-body component measuring apparatus according to claim 1, further comprising:
    a movement driving mechanism that three-dimensional moves the reflected-light measuring unit and the living body relative to each other so that a focal position of the reflected-light measuring unit is three-dimensional moved relative to the living body to obtain three-dimensional data on the inner tissue of the living body.

4. The living-body component measuring apparatus according to claim 1, wherein the analysis unit measures the component of the inner tissue on the basis of data standardized by dividing the detection signal for the reflected light from the inner tissue by the detection signal from the second light receiving element.

5. The living-body component measuring apparatus according to claim 1,
    wherein the light source incorporates a third light receiving element that monitors the laser light emitted from the light source, and
    wherein the light-source driving circuit drives the light source on the basis of at least one of the detection signal from the second light receiving element and a detection signal from the third light receiving element so that the intensity of the laser light emitted from the light source is kept at the predetermined value.

6. The living-body component measuring apparatus according to claim 1,
    wherein the light source incorporates a third light receiving element that monitors the laser light emitted from the light source, and
    wherein the analysis unit measures the component of the inner tissue on the basis of data standardized by dividing the detection signal for the reflected light from the inner tissue by at least one of the detection signal from the second light receiving element and a detection signal from the third light receiving element.

7. The living-body component measuring apparatus according to claim 1,
    wherein the light source incorporates a third light receiving element that monitors the laser light emitted from the light source, and
    wherein the analysis unit measures the component of the object on the basis of data obtained by linearly combining a first standardized signal obtained by dividing the detection signal for the reflected light from the inner tissue by the detection signal from the second light receiving element and a second standardized signal obtained by dividing the detection signal for the reflected light from the inner tissue by a detection signal from the third light receiving element.

8. The living-body component measuring apparatus according to claim 5, wherein the light-source driving circuit drives the light source on the basis of at least one of the detection signal from the second light receiving element, the detection signal from the third light receiving element, and a detection signal for the reference light so that the intensity of the laser light from the light source is kept at the predetermined value.

9. The living-body component measuring apparatus according to claim 8, wherein the analysis unit measures the component of inner tissue on the basis of data standardized by dividing the detection signal for the reflected light from the inner tissue by at least one of the detection signal from the second light receiving element, the detection signal from the third light receiving element, and the detection signal for the reference light.

10. The living-body component measuring apparatus according to claim 8, wherein the analysis unit measures the component of the inner tissue on the basis of data obtained by linearly combining signals standardized by dividing the detection signal for the reflected light from the inner tissue by the detection signal from the second light receiving element, the detection signal from the third light receiving element, and the detection signal for the reference light.

11. The living-body component measuring apparatus according to claim 1,
wherein the reflected-light measuring unit includes:
an objective lens that collects the laser light emitted from the light source and applies the laser light onto the inner tissue;
a second light collector that collects the reflected light having the optical path by changed by the beam splitter;
a second pinhole that transmits the reflected light collected by the second light collector;
a second light receiving element that receives the reflected light transmitted through the second pinhole and outputs a data signal based on an amount of the received reflected light; and
an A/D collector that subjects the data signal to A/D conversion and outputs the converted data signal to the analysis unit.

12. The living-body component measuring apparatus according to claim 6, wherein the light-source driving circuit drives the light source on the basis of at least one of the detection signal from the second light receiving element, the detection signal from the third light receiving element, and a detection signal for the reference light so that the intensity of the laser light from the light source is kept at the predetermined value.

13. The living-body component measuring apparatus according to claim 7, wherein the light-source driving circuit drives the light source on the basis of at least one of the detection signal from the second light receiving element, the detection signal from the third light receiving element, and a detection signal for the reference light so that the intensity of the laser light from the light source is kept at the predetermined value.

14. A living-body component measuring apparatus that measures a component of an inner tissue of a living body serving as an object to be measured, the living-body component measuring apparatus comprising:
a light source emitting laser light having two or more wavelengths;
a branching unit that branches the laser light emitted from the light source;
a reference-light measuring unit that measures, as reference light, one part of the laser light branched by the branching unit into a first direction;
a reflected-light measuring unit that measures the other part of the laser light branched by the branching unit into a second direction different from the first direction and serving as a reflected light of the laser light from the inner tissue of the living body;
an analysis unit that analyzes the inner tissue of the living body by measuring a spectrum of the reflected light and the reference light serving as the part of the laser light branched by the branching unit;
an optical fiber that is configured to apply the laser light emitted from the light source onto a surface of the living body;
a second light receiving element that detects reflected light of the laser light applied by the optical fiber in a third direction different from the first and second directions, the reflected light being reflected by the surface of the living body; and
a light-source driving circuit that drives the light source on the basis of a detection signal from the second light receiving element so that an intensity of the laser light emitted from the light source is kept at a predetermined value.

15. A living-body component measuring apparatus that measures a component of an inner tissue of a living body serving as an object to be, the living-body component measuring apparatus comprising:
a light source emitting laser light having two or more wavelengths;
a first beam splitter that transmits one part of the laser light emitted from the light source in a first direction and changes an optical path of the other part of the laser light into a second direction different from the first direction;
a second beam splitter that changes an optical path of the part of the laser light incident through the first beam splitter in the first direction, transmits the other part of the laser light in the first direction, and changes an optical path of a reflected light of the laser light from the inner tissue of the living body into a third direction different from the first direction;
a reference-light measuring unit that measures, as reference light, the other part of the laser light having the optical path changed by the first beam splitter in the second direction towards the reference-light measuring unit;
a reflected-light measuring unit that measures the reflected light reflected by the inner tissue of the living body and having the optical path changed by the second beam splitter in the third direction towards the reflected-light measuring unit;
an analysis unit that analyzes the inner tissue of the living body by measuring a spectrum of the reflected light and the reference light having the optical path changed by the first beam splitter;
an optical fiber that is configured to apply the laser light emitted from the light source onto a surface of the living body;
a second light receiving element that detects reflected light of the laser light applied by the optical fiber in a fourth direction different from the first, second and third directions, the reflected light being reflected by the surface of the living body; and
a light-source driving circuit that drives the light source on the basis of a detection signal from the second light receiving element so that an intensity of the laser light emitted from the light source is kept at a predetermined value.

\* \* \* \* \*